United States Patent [19]
Victor et al.

[11] Patent Number: 5,862,832
[45] Date of Patent: Jan. 26, 1999

[54] GRADIENT PROPORTIONING VALVE

[75] Inventors: Richard Victor, Mendon; Robert J. Dumas, Upton; William W. Carson, Hopkinton, all of Mass.

[73] Assignee: Waters Investments Limited, New Castle, Del.

[21] Appl. No.: 609,086

[22] Filed: Feb. 29, 1996

[51] Int. Cl.⁶ .................................................. F16K 11/00
[52] U.S. Cl. ............................................. 137/606; 138/30
[58] Field of Search .................................. 137/606, 607; 138/30

[56] References Cited

U.S. PATENT DOCUMENTS

| | | | |
|---|---|---|---|
| 2,902,988 | 9/1959 | Rippingille | 138/30 X |
| 3,327,729 | 6/1967 | Erickson | 137/606 X |
| 4,383,551 | 5/1983 | Lynch et al. | 137/606 X |
| 4,595,496 | 6/1986 | Carson | 210/101 |
| 5,494,076 | 2/1996 | Knapp | 138/30 X |

*Primary Examiner*—Stephen M. Hepperle
*Attorney, Agent, or Firm*—Brian Michaelis; Anthony J. Janiuk

[57] ABSTRACT

An improved gradient proportioning valve compensates for hydraulic inertia in a compact, reliably sealed valve assembly that is less susceptible to unswept volumes and gas permeation. A flat diaphragm is located within an accumulator volume integral to a valve manifold block. The compliance and damping of the diaphragm are optimized for the application's flow characteristics. Sealing of the diaphragm is provided by a sealing plug installed in the manifold block. The diaphragm has only one sealing joint. The sealing plug configuration allows for a more reliable clamping and sealing of the diaphragm which reduces and substantially eliminates the potential for leaks. Potential for unswept volumes is substantially eliminated by including the accumulator volume as a unitary part of the valve manifold. Air permeation into the fluid stream is substantially reduced by a reduction in surface area and exposed liquid volume in the accumulator, effected by including the accumulator volume as part of the valve manifold. Valve size is decreased by the elimination of the external tube accumulators and associate fittings. The valve that is more conducive to use and attainment of the benefits of in-line solvent degassing. More accurate delivery of the respective proportions of components of a liquid composition is achieved. Pump flow is positively impacted.

15 Claims, 2 Drawing Sheets

GRADIENT PROPORTIONING VALVE

FIELD OF THE INVENTION

The present invention relates to liquid composition control, and more particularly to an improvement in a valve delivering fluid components in proper proportions to a pump, such as in a high performance liquid chromatography (HPLC) system.

BACKGROUND

Valves are known for use in systems for low pressure metering and delivery of components of a liquid composition in systems, such as HPLC systems, that require accurate proportioning of components of the liquid composition. U.S. Pat. No. 4,595,496 ("the '496 patent"), which is hereby incorporated herein by reference, describes various known implementations for addressing applications which require mixing liquids in controlled proportions. The '496 patent discloses and claims a novel system including a switching valve arrangement to the inlet of a high pressure pump for delivery of liquid in an HPLC system.

The invention in the '496 patent overcomes limitations and disadvantages of the prior art by providing a system, suitable for use in liquid chromatography applications, in which problems associated with the non-uniformity of the draw stroke of an HPLC pump and fluid inertia of the solvent delivery system are minimized with a concomitant minimal impact on system design and cost. This is accomplished by connecting a plurality of reservoirs, each containing a liquid to be mixed to form a liquid composition, through a switching valve arrangement to the inlet of a high pressure pump for ultimate delivery to an HPLC column.

As described in the '496 patent, a flow and composition controller actuates the switching valves in a manner that allows the non-uniformity of the draw stroke of the pump to be equally shared by each of the liquid components over several cycles of switching valve actuation. A microprocessor drives both the pump and the fluid switching valves and includes means for generating a ratio between the time to connect all of the reservoirs selected for actuation and the cycle time for a pump draw stroke. By connecting the output of the pump drive to the valve drive, this ratio is held constant throughout the operation of the chromatographic system within a given flow range.

To avoid problems associated with the non-uniformity of the volumetric intake rate, according to the '496 patent, it had been found advantageous to establish the relationship, i.e. ratio, between the pump cycle time and the switching valve cycle time as a non-integer ratio that could be either greater than or less than one. The result was an averaging of the non-uniformity of the pump intake rate over many switching valve cycles, effecting compositional averaging that produced a more accurate mixture after several draw strokes.

The implementation of the non-integer ratio relationship between the pump cycle time and the switching valve cycle time created other concerns related to the affects on compositional accuracy resulting from the valves being actuated at widely varying pump intake rates. In particular, switching a valve open or closed during the rapid intake portion of the pump draw stroke, ideally, should cause instantaneous changes in flow through the valve. However, hydraulic inertia associated with the fluid in the relatively long length of tubing between the solvent reservoir and the valve resisted instantaneous flow changes. This resulted in inaccurate and unpredictable compositions which were highly dependent on specific operating conditions such as flow rate, tubing length, tubing diameter, tubing stiffness, solvent density, solvent compressibility, etc. These problems became magnified at high flow rates and/or short duration valve actuations, particularly in systems designed to operate over wide dynamic ranges of flow rate and solvent composition.

According to the '496 patent, and as illustrated in FIG. 1 herein (corresponding to FIG. 5 of the '496 patent with the reference numerals in accordance therewith), the hydraulic inertia related problems were addressed by implementing a series of hydraulic accumulators, one for each reservoir, directly adjacent to the switching valve arrangement 17A, 17B on the side closest to the reservoirs, i.e. the low pressure side of the system. The accumulators 19A, 19B allowed the fluid flow through the valves to accurately correspond to the rate of volume displacement during the pump draw stroke. Each accumulator 19A, 19B consisted of a soft-walled, flexible plastic tube 50 of generally circular cross-section. The accumulator tube 50 was adapted at an end closest to the valve inlet to snugly slide over a rigid plastic connector 52. A connecting tube 54 was implemented at the opposite end of the accumulator tube to hold the relatively long length of flow tubing 56 that connects the valves with the reservoirs. The end of the accumulator tube adjacent the connecting tube was caused to assume approximately the cross-section of a flattened ellipse 55 which allowed a significant internal volume change to occur in the accumulator tube, with little change in pressure thereby allowing the accumulator to overcome the effects of hydraulic inertia.

However, the implementation of such accumulator tubes is not without its own set of problems. The addition of accumulator tubes significantly increases the amount of space required to house the valve switching assembly. Sufficient space has to be provided to accommodate the tubes unhindered, e.g. without kinks or other restrictions.

The accumulator tubes each require interconnections at two ends, which presents the potential for unreliable sealing in the system. Inadequate seals at either end of the tubes results in leaks in the system for fluid to escape or for air to enter the system.

In addition to the potential for air to permeate the system at the exposed sealing points of the accumulator tubes, the large surface area of the tubes themselves are permeable, permitting air to enter the system. Air permeating the system and entering the solvent will cause pump flow errors. The problem created by the permeability of the tubes is exacerbated in systems where in-line solvent degassing is effected.

Furthermore, the accumulator tubes present areas for the collection of unswept volumes, that is, volumes of solvent that are not easily swept from the accumulator tubes. Unswept volumes will retain air bubbles, reducing the accuracy of the flow performance. Unswept volumes result in residual solvent components that require more time to clear the system and change between solvents. The accumulator tubes present the occurrence of unswept volumes which are difficult to eliminate, especially at the tubing joints.

SUMMARY OF THE INVENTION

The present invention provides an improved gradient proportioning valve switching mechanism which compensates for hydraulic inertia in a compact, reliably sealed valve assembly that is less susceptible to unswept volumes and gas permeation.

According to the invention, accumulator tubes of the prior art are replaced by a flat diaphragm which is located within an accumulator volume integral to a valve manifold block. The compliance and damping of the diaphragm are optimized for the application's flow characteristics. Sealing of the diaphragm is provided by a sealing plug installed in the manifold block. The diaphragm has only one sealing joint, compared with the several required for the prior art accumulator tubes.

The sealing plug configuration allows for a more reliable clamping and sealing of the diaphragm which reduces and substantially eliminates the potential for leaks. The potential for unswept volumes is substantially eliminated by including the accumulator volume as a unitary part of the valve manifold. Air permeation into the fluid stream is substantially reduced by a reduction in surface area and exposed liquid volume in the accumulator, effected by including the accumulator volume as part of the valve manifold. Valve size is decreased by the elimination of the external tube accumulators and associate fittings.

Further features and advantages of the present invention include provision of a valve that is more conducive to use and attainment of the benefits of in-line solvent degassing. More accurate delivery of the respective proportions of components of a liquid composition is achieved with a valve according to the invention. Pump flow is positively impacted.

Still other features, advantages and aspects of the present invention will become apparent from a description of illustrative embodiments hereinafter, when read in conjunction with the drawings.

DETAILED DESCRIPTION

A gradient proportioning valve accommodates the flow of fluids from external reservoirs into the valve for mixing in appropriate proportions to form a liquid composition, as understood by those skilled in the art. In an actual embodiment, such a valve would typically include four inlet valves ported to a common outlet. In terms of functionality, again as known in the art, each inlet valve is a normally closed, solenoid actuated diaphragm valve that is switched in a controlled manner to provide the appropriate amount of fluid required in mixing the liquid composition. The function of the overall valve is to provide a continuous stream of a compositionally accurate mixture of components, such as solvents in an HPLC implementation. The mixture must be provided from the common outlet under flowing conditions, while not interfering with the flow rate of the fluid input stream, and without changing or otherwise affecting the quality/composition of the fluids input for mixing.

Figure 1:
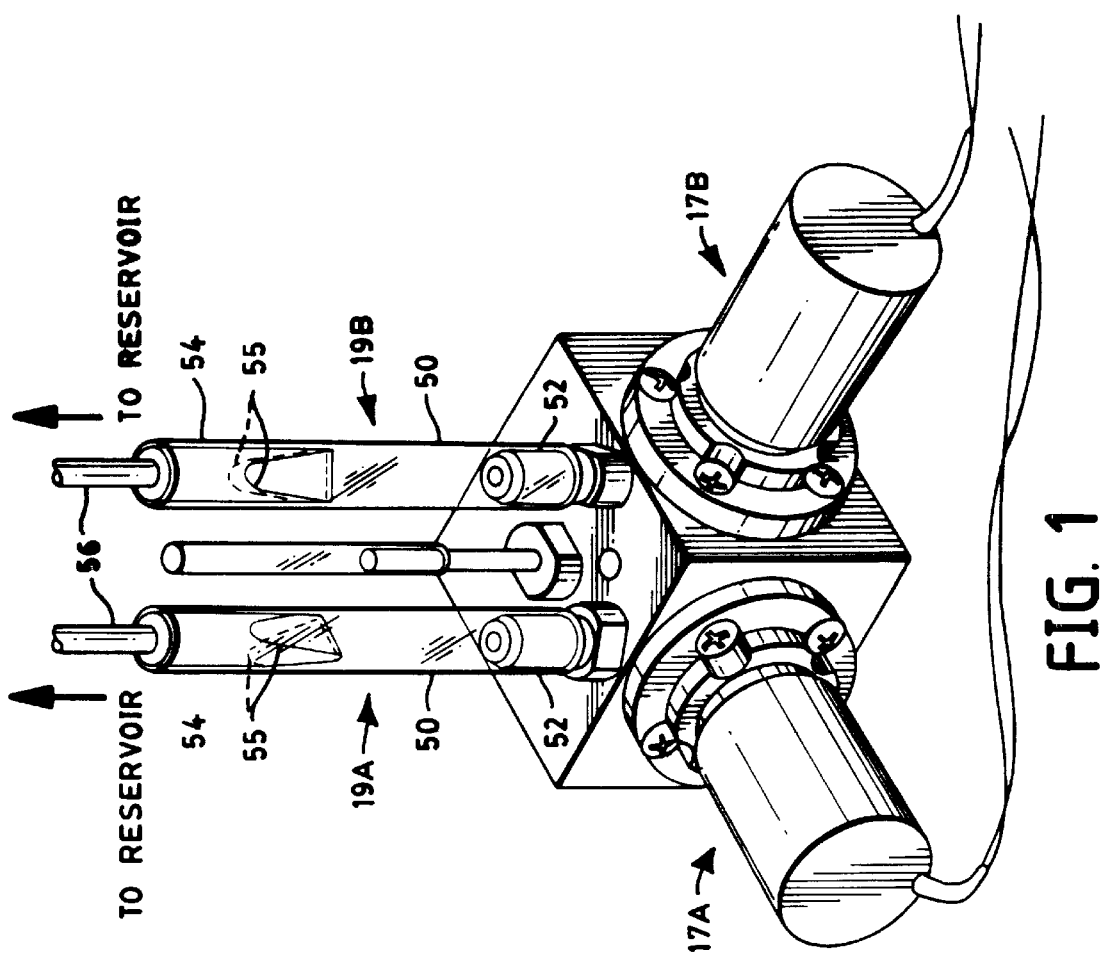
FIG. 1 is an illustration of accumulator tubes according to the prior art, implemented to overcome problems associated with hydraulic inertia.
Figure 2:
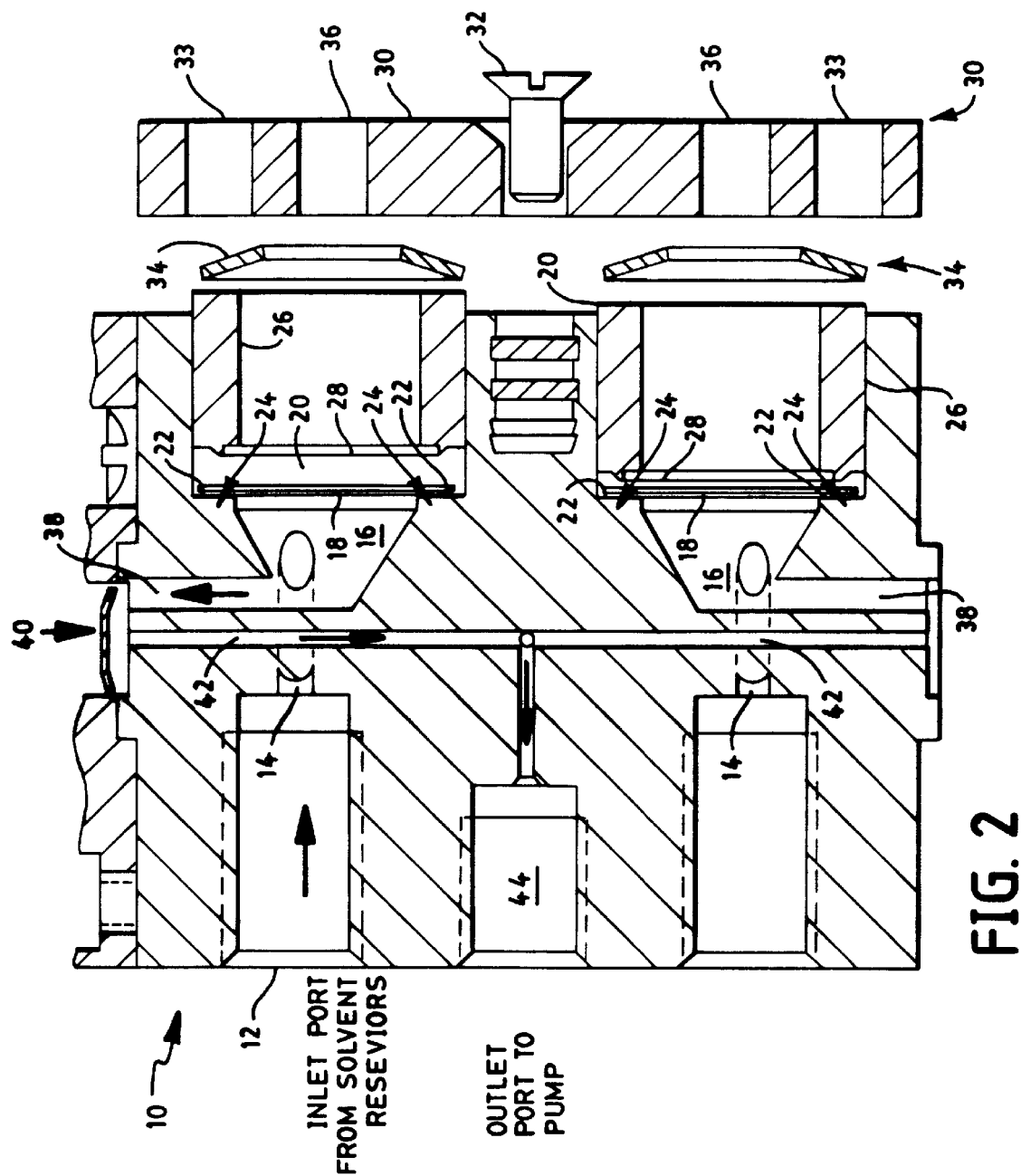
FIG. 2 is a sectioned view of an improved gradient proportioning valve implemented with an accumulator diaphragm according to the invention.

Referring now to FIG. 2, a gradient proportioning valve according to the invention is configured having a valve manifold 10 that accommodates the flow of fluids from external reservoirs (not shown). For the sake of clarity of the discussion hereinafter, the illustrative valve described herein has the capacity to mix only two input fluid streams. The input fluid streams to be mixed are received from the reservoirs and are introduced into the valve at inlet ports 12. Fluids from the respective reservoirs, such as solvents used in HPLC as known in the art, flow into respective inlet ports 12 and thereafter flow through respective inlet conduits 14 in the manifold 10 into respective accumulator volumes or chambers 16.

The integral accumulator chambers 16, as well as the inlet ports 12 and inlet conduits 14, are appropriately dimensioned as a function of the flow rate of the valve application. The chamber 16 is frustum-shaped having a conical-base opposed to the inlet conduit 14. The chamber is shaped to maximize the surface area of the diaphragm (for compliance), and the inlet conduit 14 is positioned to allow for the best swept volume geometry. Accordingly, the chamber 16 also has a smooth transition from larger to smaller cross-section. The placement of the chamber is such that the fluidic resistance between the valve diaphragm (FIG. 2, 40 discussed hereinafter) and the accumulator is minimized. Fluid flowing through the conduit 14 flows perpendicular to the conical-base, into the chamber 16 to confront the base or back of the chamber 16.

An accumulator diaphragm 18 is positioned at the conical-base or back of the chamber 16, opposite the inlet conduit 14. The diaphragm 18 in this illustrative embodiment, is a 0.002 inch thick film formed of Polytetrafluoroethylene (PTFE) laminated on each side with Fluorinated Etylene Propylene (FEP). Type DF-1700-DB heat bondable cast tape available from Chemical Fabrics Corporation, Merrimack N.H., is used in the present implementation.

The diaphragm, as with all components in the fluid path of the present illustrative embodiment, is formed of materials that are functionally unaffected by a full range of organic solvents and aqueous solutions of acids, bases, salts, surfactants, etc. and other phase modifiers that may be used in any mode of liquid chromatography. The diaphragm 18 effects a membrane or compliant member at the back of the accumulator chamber 16 to allow internal volume changes in the chamber to occur with little change in pressure. Accordingly, as with the less advantageous accumulator tubes of the prior art, the valve can overcome the effects of hydraulic inertia. The compliance and damping of the diaphragm are optimized for the applications flow characteristics, as will be appreciated by those skilled in the art.

An oversized bore 20 behind the back of the conical-base or back of the accumulator chamber 16 is configured to receive the diaphragm 18 for clamping and sealing the diaphragm tightly therein. A seating surface 22 interior to the bore 20 provides an abutment against which the diaphragm seats. A sealing groove 24 is disposed in the seating surface 22 and provides a portion of the single seal effected in the implementation according to the invention. A cylindrical sealing plug 26 formed of stainless steel, includes a sealing ridge 28 that fits tightly into the sealing groove 24 to seal the diaphragm in the bore 20 when the plug 26 is engaged against the seating surface 22 with the diaphragm sandwiched therebetween.

Preferably, the sealing plug 26 is dimensioned to fit snugly, yet slidably within the bore 20. The plug 26 is held in place by a clamping plate 30 which is mechanically attached to the valve manifold such as by a screw 32. Additional mounting holes 33 are provided in the clamping plate 30 to facilitate the mechanical fastening of the clamping plate to the valve manifold 10. In this illustrative embodiment, resilient members such as belville springs 34 or washers are disposed between the sealing plug 26 and the clamping plate 30, to provide some resiliency.

The diaphragm according to the invention overcomes hydraulic inertia while minimizing the volume of fluid in the valve that is exposed to potential air permeation, by limiting the surface area of the diaphragm that is exposed to ambient air. In contrast to the prior art wherein the entirety of the accumulator tubes were exposed and the volumes of fluid therethrough subjected to ambient air permeating the tubes, the diaphragm according to the present invention is only exposed to ambient in a limited manner. Atmospheric ports 36 are provided in the clamping plate 30 to permit ambient air at the back of the diaphragm 18. While exposure to ambient air is necessary for the diaphragm to perform its intended function, the reduced surface area exposed within the atmospheric ports significantly limits permeation of air through the diaphragm.

As briefly described hereinbefore, input fluid streams to be mixed are received from reservoirs and are introduced into the valve manifold 10 at inlet ports 12. Fluids from the respective reservoirs flow into respective inlet ports 12 and thereafter flow through respective inlet conduits 14 in the manifold 10 into respective accumulator volumes or chambers 16.

In the respective integral accumulator chambers 16 the fluids to be mixed encounter the compliant diaphragm which allows internal volume changes in the chambers to occur with little change in pressure so that the valve can overcome the effects of hydraulic inertia. The fluids to be mixed flow out of the chambers 16 through chamber ports 38 whereupon the fluids are available at switched valve diaphragms 40. The valve diaphragms are reciprocated by switched valves as known in the art. The controlled switching of the valve diaphragms determines the proportion of a respective fluid that is received in a common port 42 within the valve manifold 10. The respective fluids are mixed in their respective proportions in the common port 42 and are available at an outlet port 44 for downstream processing as known in the art.

Although only a two input valve is described in the illustrative embodiment herein, it will be appreciated that the concepts according to the invention could be implemented in a valve having any number of inlet ports for mixing a liquid composition.

While the diaphragm described herein is formed of FEP-PTFE-FEP laminated, it will be appreciated that other materials can be implemented to effect a diaphragm, such as thin stainless steel, various composite materials, rubber or the like.

Although the sealing plug in the illustrative embodiment is a cylindrical plug formed of stainless steel, it will be appreciated that alternative sealing mechanisms can be implemented while permitting ambient pressure at the back of the diaphragm, such as spongy materials, cylindrically shaped composite material or the like. Furthermore, while the sealing plug effects a tight seal by having a sealing ridge that seats in a sealing groove in a bore receiving the plug, it will be appreciated that the groove could be in the plug and the ridge on a surface of the bore.

Although the invention has been shown and described with respect to an exemplary embodiment thereof, it will be appreciated the foregoing and various other changes, omissions and additions in the form and detail thereof may be made therein without departing from the spirit and scope of the invention.

What is claimed is:

1. An improved fluid mixing valve receiving a plurality of fluids into a respective plurality of inlet ports to a valve manifold for mixing said plurality of fluids in a controlled manner in a common port to provide a fluid composition at a common outlet port, wherein the improvement comprises:

a plurality of conduits internal to said valve manifold, each of said plurality of conduits receiving fluid through a respective one of said respective plurality of inlet ports;

a plurality of accumulator chambers internal to said valve manifold each of said plurality of accumulator chambers receiving fluid through a respective one of said plurality of conduits, each of said plurality of accumulator chambers having a diaphragm disposed therein, a first side of said diaphragm exposed to an interior of a respective accumulator chamber and a second side of said diaphragm exposed to an exterior of said valve manifold; and a plurality of chamber outlets each of said plurality of chamber outlets being in communication with a respective one of said plurality of accumulator chambers and selectively in communication with said common port.

2. The valve of claim 1 wherein said diaphragm is retained in said respective accumulator chamber by a sealing plug that is configured to permit said second side of said diaphragm to be exposed to said exterior of said valve manifold.

3. The valve of claim 1 wherein said diaphragm is retained in said respective accumulator chamber by a cylindrical sealing plug inserted in a bore.

4. The valve of claim 3 wherein said bore includes a seating surface having a sealing groove disposed therein and a surface of said cylindrical sealing plug includes a sealing ridge configured to fit within said sealing groove.

5. The valve of claim 2 wherein said sealing plug is maintained in engagement with said valve manifold by a clamping plate.

6. The valve of claim 5 wherein a resilient member is disposed between said sealing plug and said clamping plate.

7. The valve of claim 1 wherein said diaphragm is a laminated member comprised of PTFE and FEP.

8. A valve, comprising:

a valve manifold;

an inlet port to said valve manifold;

a conduit internal to said valve manifold and configured to receive fluid through said inlet port;

an accumulator chamber internal to said valve manifold and configured to receive fluid through said conduit;

a diaphragm disposed in a base portion of said accumulator chamber, said diaphragm having a first side exposed to an interior of said accumulator chamber and a second side exposed to an exterior of said valve manifold; and a chamber outlet configured to transport fluid from said accumulator chamber to the exterior of said valve manifold.

9. The valve of claim 8 wherein said accumulator chamber is a frustum-shaped chamber and said base is a conical-base of said frustum-shaped chamber and said diaphragm is disposed at said conical-base.

10. The valve of claim 8 wherein said diaphragm is retained in said accumulator chamber by a sealing plug that is configured to permit said second side of said diaphragm to be exposed to said exterior of said valve manifold.

11. The valve of claim 8 wherein said diaphragm is retained in said accumulator chamber by a cylindrical sealing plug inserted in a bore.

12. The valve of claim 11 wherein said bore includes a seating surface having a sealing groove disposed therein and a surface of said cylindrical sealing plug includes a sealing ridge configured to fit within said sealing groove.

13. The valve of claim 10 wherein said sealing plug is maintained in engagement with said valve manifold by a clamping plate.

14. The valve of claim 13 wherein a resilient member is disposed between said sealing plug and said clamping plate.

15. The valve of claim 8 wherein said diaphragm is a laminated member comprised of PTFE and FEP.

* * * * *